(12) United States Patent
Nakanishi

(10) Patent No.: US 8,579,629 B2
(45) Date of Patent: Nov. 12, 2013

(54) DENTAL HANDPIECE

(75) Inventor: Eiichi Nakanishi, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 0 days.

(21) Appl. No.: 13/483,250

(22) Filed: May 30, 2012

(65) Prior Publication Data

US 2012/0308958 A1 Dec. 6, 2012

(30) Foreign Application Priority Data

Jun. 1, 2011 (JP) ................................ 2011-123783

(51) Int. Cl.
*A61C 1/05* (2006.01)
(52) U.S. Cl.
USPC ......................................................... 433/115
(58) Field of Classification Search
USPC ......... 433/114, 115, 116, 120, 126, 130, 131, 433/132, 133, 125
See application file for complete search history.

(56) References Cited

U.S. PATENT DOCUMENTS

| | | | | |
|---|---|---|---|---|
| 2,041,077 A * | 5/1936 | Lininger | ........................ | 433/116 |
| 3,324,552 A * | 6/1967 | Saffir | ............................. | 433/82 |
| 3,542,372 A * | 11/1970 | Edwardson | .................... | 277/309 |
| 4,295,830 A * | 10/1981 | Uchida | .......................... | 433/115 |
| 4,369,034 A * | 1/1983 | Garnier et al. | ................. | 433/115 |
| 5,078,601 A * | 1/1992 | Badoz et al. | ..................... | 433/82 |
| 5,352,118 A * | 10/1994 | Franetzki et al. | ............... | 433/82 |
| 5,964,590 A | 10/1999 | Loddeke et al. | | |
| 6,315,559 B1 * | 11/2001 | Nakanishi | ...................... | 433/125 |
| 8,092,217 B2 * | 1/2012 | Zhang | ............................ | 433/115 |
| 2008/0213722 A1* | 9/2008 | Hofer | ............................. | 433/131 |
| 2010/0227293 A1 | 9/2010 | Kimura et al. | | |
| 2011/0171594 A1* | 7/2011 | Tosetti et al. | .................. | 433/116 |

FOREIGN PATENT DOCUMENTS

| | | |
|---|---|---|
| DE | 44 11 054 C1 | 8/1995 |
| EP | 2 226 032 A1 | 9/2010 |
| JP | 11-290342 A | 10/1999 |

* cited by examiner

*Primary Examiner* — Ralph Lewis
(74) *Attorney, Agent, or Firm* — Jason D. Voight

(57) ABSTRACT

A dental handpiece is disclosed which has a head housing, a gear shaft having a gear part with gear teeth and a shaft part extending from the gear part, and a dust control seal sealingly fit on the circumferential surface of the shaft part of the gear shaft. The dust control seal is an annular member, and has a seal body, a first lip projecting radially inwardly from the seal body, and a second lip projecting radially inwardly from the seal body above and spaced apart from the first lip, with a space defined between a contact area between the first lip and the shaft part, and a contact area between the second lip and the shaft part.

4 Claims, 4 Drawing Sheets

DENTAL HANDPIECE

FIELD OF ART

The present invention relates to a dental handpiece, in particular, a dental handpiece having an improved gear shaft assembled in the head section to hold a dental treatment tool, and an improved dust control seal attached to the gear shaft.

BACKGROUND ART

There are known a dental handpiece having a head section accommodating a bur sleeve in which a dental treatment tool is held, a neck section containing a power transmission shaft, a grip section containing a rotary shaft, and a drive section containing a motor, which sections are connected to each other proximally in this order. Drive of the motor is transmitted via the rotary shaft and the power transmission shaft, and rotates the bur sleeve at high speed.

A conventional handpiece of this type is shown in FIG. 5. A handpiece H has a head 51a for drivingly holding a treatment tool therein, and a neck 51b extending proximally from the head 51a, which two are formed integrally and referred to collectively as a head-neck section 52. To the proximal end of the head-neck section 52, a grip section (not shown) is detachably connected.

The head 51a has a generally cylindrical head housing 54, a gear shaft 55 accommodated in the head housing 54, and a retaining member 56 for rotatably retaining the gear shaft 55 in the head housing 54 as a bearing. The gear shaft 55 is composed of a gear part 57 which has teeth extending upwards and arranged circumferentially in a horizontal plane, and a shaft part 58 extending downwards from the gear part 57 and made of stainless steel. A dust control seal 59 is fit on the shaft part 58 below the retaining member 56, and a cap 62 is fit on the dust control seal 59 to fix the seal 59 and the retaining member 56 in the housing 54.

The dust control seal 59 is a generally annular member having a seal body 60 and an annular lip 61 projecting radially inwardly from the seal body 60 and having a tapered cross section. When external force is applied to the thinned edge of the lip 61, the lip 61 is elastically deformed to sealingly hold the dust control seal 59 against the circumference of the shaft part 58 of the gear shaft 55.

A dental handpiece of this type is disclosed in, for example, JP-11-290342-A.

With the sealing mechanism of such a conventional dust control seal, dust such as tooth debris or abrasive powders tends to enter the contact area between the shaft part 58 of the gear shaft 55 and the dust control seal, and abrades the circumference of the shaft part 58. This may cause entry of dust further into the head housing to damage the gear and lead to rotation instability.

SUMMARY OF THE INVENTION

It is an object of the present invention to provide a dental handpiece which has improved dust control function in the head section, and is hard to have troubles.

According to the present invention, there is provided a dental handpiece comprising:
a head housing,
a gear shaft accommodated in the head housing, and having a gear part with gear teeth and a shaft part extending from said gear part, and
a dust control seal sealingly fit on a circumferential surface of said shaft part of the gear shaft,
wherein said dust control seal is an annular member, and has a seal body, a first lip projecting radially inwardly from the seal body, and a second lip projecting radially inwardly from the seal body above and spaced apart from said first lip,
wherein said first and second lips define a space between a contact area between the first lip and the shaft part and a contact area between the second lip and the shaft part.

The dental handpiece may further comprise a retaining member for rotatably retaining said gear shaft in the head housing, and
a fixing member for fixing the retaining member in the head housing,
wherein said dust control member is held between the retaining member and the fixing member.

The dust control seal may be made of a rubber material.

The shaft part of the gear shaft may be provided with hard coating, in particular selected from the group consisting of diamond-like carbon (DLC), CrN, TiN, and TiCN.

PREFERRED EMBODIMENTS OF THE INVENTION

Figure 1:
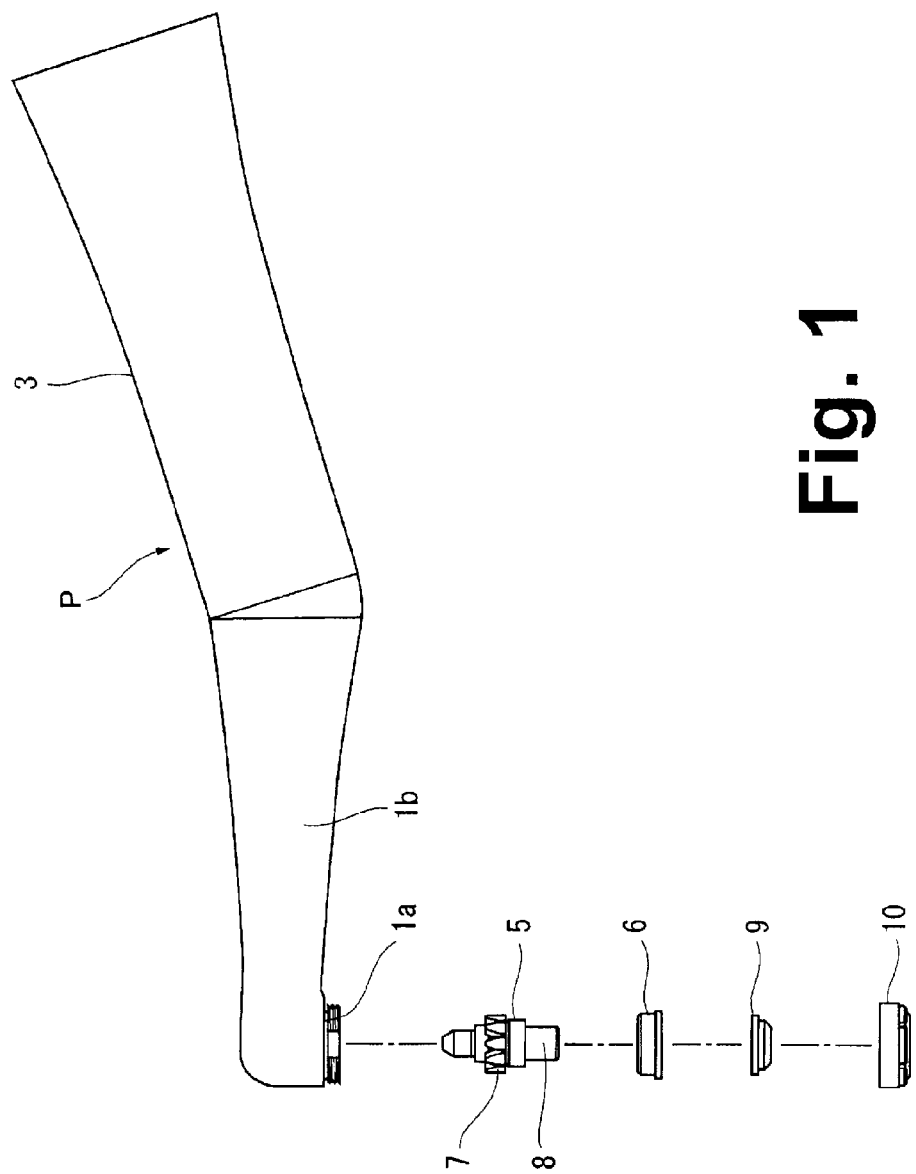
FIG. 1 is a partially exploded side view of a dental handpiece according to an embodiment of the present invention.
Figure 2:
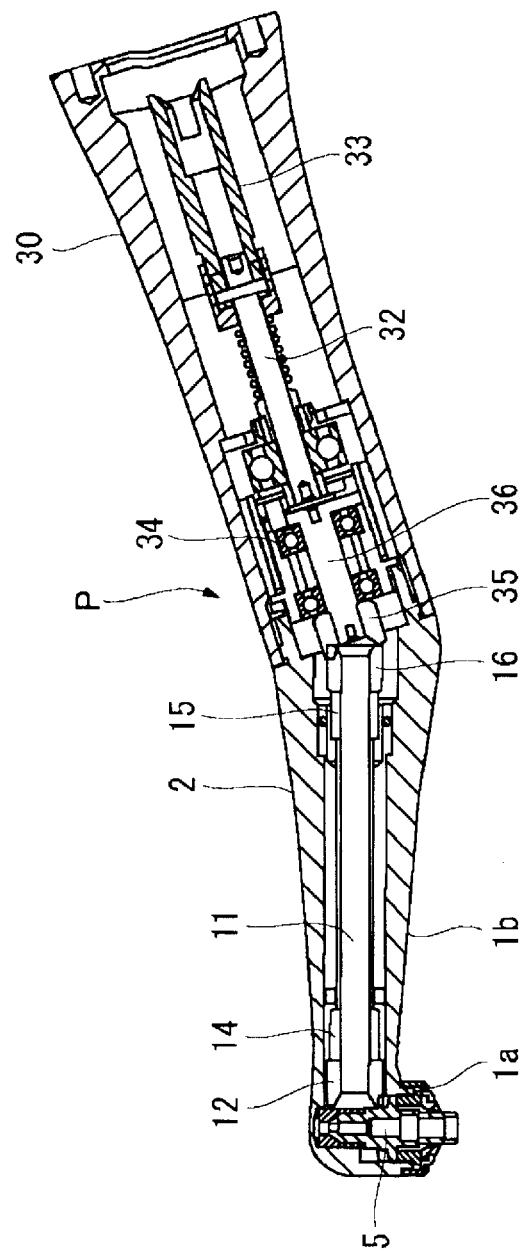
FIG. 2 is a longitudinal sectional view of the dental handpiece of FIG. 1, showing the internal structure.
Figure 3:
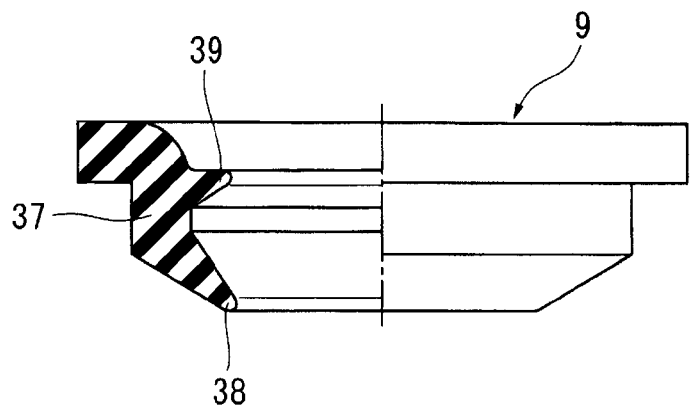
FIG. 3 is a partially sectioned front view of a dust control seal in the handpiece of FIG. 1.
Figure 4:
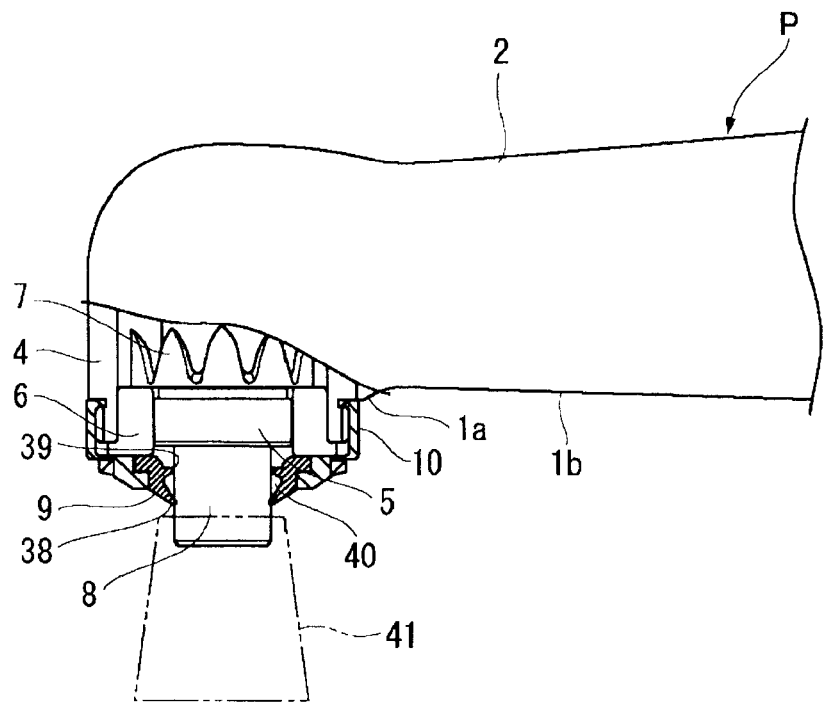
FIG. 4 is a partially sectioned side view of the head section of the handpiece of FIG. 1, showing the internal structure.
Figure 5:
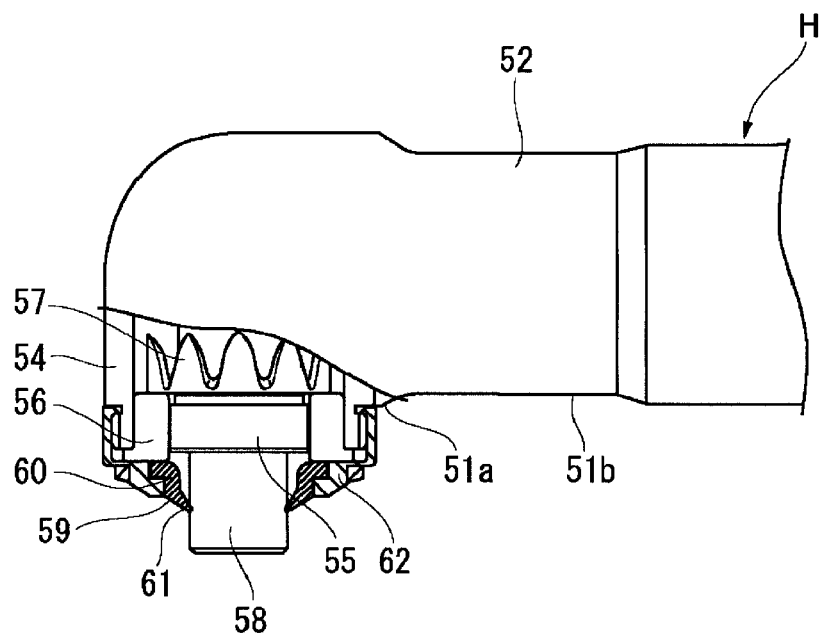
FIG. 5 is a partially sectioned side view of the head section of a conventional dental handpiece.

The present invention will now be explained in detail with reference to the attached drawings, wherein FIG. 1 shows the overall structure of the dental handpiece according to the present invention, and FIGS. 2 to 4 show the internal structure or various part structures of the handpiece.

Referring to FIG. 1, a dental handpiece P has a head 1a for drivingly holding a treatment tool therein, and a neck 1b extending proximally from the head 1a and generally cylindrically, which two are formed integrally as a head-neck section 2. The handpiece P further has a generally cylindrical grip section 3 detachablly connected to the proximal end of the head-neck section 2, and a drive unit (not shown) detachably connected to the proximal end of the grip section 3.

Referring to FIG. 4, the head 1a has a generally cylindrical head housing 4, a gear shaft 5 accommodated in the head housing 4, and a retaining member 6 for rotatably retaining the gear shaft 5 in the head housing 4. The retaining member 6 functions as a bearing for the gear shaft 5. The gear shaft 5 has a gear part 7 which has teeth extending upwards and arranged circumferentially in a horizontal plane, and a shaft part 8 extending downwards from the gear part 7. The shaft part 8 may preferably be provided with a hard coating of, for example, DLC (diamond-like carbon), CrN (chromium nitride), TiN (titanium nitride), or TiCN (titanium carbon nitride). A dental treatment tool 41 is attached to the shaft part 8. A dust control seal 9 is fit on the shaft part 8 below the retaining member 6, and a cap 10 is fixed to the housing 4 to fix the retaining member 6 and the seal 9 held between the cap 10 and the retaining member 6 in the housing 4.

Referring to FIG. 2, a shaft 11 is disposed extending through the neck 1b of the head-neck section 2 as a power transmission member, and provided on its distal end with an output gear 12, which meshes with the gear part 7 of the gear shaft 5. The axis of the shaft 11 crosses the axis of the gear shaft 5, for example at right angles, and the gear part 7 and the output gear 12 constitute a power transmission mechanism like bevel gears. On the proximal end of the shaft 11 is provided an input gear 16. The shaft 11 is sheathed in a cylindrical retainer member, and rotatably supported near both ends by metal bearings 14 and 15.

The grip section 3 has a generally cylindrical grip housing 30, a rotary shaft 32 extending through the grip housing 30, a coupling member 33 attached to the drive-source side of the rotary shaft 32, a deceleration part 34 disposed on the neck 1b side of the rotary shaft 32, and an output gear 35 provided adjacent to the deceleration part 34 on the neck 1b side. The rotary shaft 32 is connected to the coupling member 33 on the drive-source side, and operatively connected to the deceleration part 34 on the neck 1b side. The deceleration part has an output shaft 36, which has on its distal end the output gear 35. The output gear 35 on the output shaft 36 meshes with the input gear 16 on the shaft 11, with the former driving and the latter being driven. The coupling member 33 is operatively connected to a drive unit, such as a motor.

The characteristic feature of the present invention is in the head 1a. The dust control seal 9 fit around the gear shaft 5 is made of an elastic material, such as fluororubber or silicon rubber. As shown in FIG. 3, the dust control seal 9 is a generally annular member, and has a seal body 37, a first lip 38 projecting radially inwardly from the lower part of the seal body 37, and a second lip 39 projecting radially inwardly from the seal body 37 above and spaced apart from the first lip 38. Both first and second lips 38 and 39 have a tapered cross section, that is, the lips 38 and 39 are thicker in the part connected to the seal body 37, and gradually become thinner toward the radially inner edges. The first and second lips 38 and 39 are arranged such that, with the dust control seal 9 sealingly held on the circumferential surface of the shaft part 8 of the gear shaft 5, a space 40 (FIG. 4) is defined between the contact area between the first lip 38 and the shaft part 8 and the contact area between the second lip 39 and the shaft part 8. Thus when external force is applied to the inner edges, the first and second lips 38, 39 are elastically deformed with a space maintained between the two.

The operation of the dental handpiece having the above structure is explained below with particular reference to FIG. 2.

Drive from the drive unit, in particular from a motor therein, is input to the coupling member 33, and transmitted to the rotary shaft 32. The rotation of the rotary shaft 32 is decelerated at the deceleration part 34, and transmitted to the shaft 11 in the neck 1b via the meshing engagement between the output gear 35 and the input gear 16. The rotation of the shaft 11 in turn causes the gear shaft 5 to rotate via the meshing engagement between the output gear 12 and the gear part 7 of the gear shaft 5, which is an input gear, to thereby rotate the treatment tool 41 attached to the shaft part 8 of the gear shaft 5.

In dental treatment, the treatment tool 41 may contact patient's teeth while it is rotating, which may cause dust such as matter deposited on teeth, tooth debris, or abrasive powders, to adhere to the shaft part 8 of the gear shaft 5. This dust may reach the contact area between the first lip 38 and the shaft part 8, and act as if it rubs the shaft part 8.

With the dental handpiece according to the present invention, since the shaft part 8 of the gear shaft 5 may be provided with a hard coating, the shaft part 8 may be prevented from being worn by the dust in the contact area between the shaft part 8 and the dust control seal 9. Part of the dust which has reached this contact area may possibly enter through this contact area into the gear shaft 5, but the space between the first and second lips 38 and 39 greatly inhibit such entry of the dust.

With such a structure, the gear shaft 5 is protected from damage or clogging with dust, and may be operated for a prolonged period of time. Thus the dental handpiece has improved dust control function in the head section, and is hard to have troubles.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece comprising:
a head housing,
a gear shaft accommodated in the head housing, and having a gear part with gear teeth and a shaft part extending from said gear part,
a dust control seal sealingly fit on a circumferential surface of said shaft part of the gear shaft,
a retaining member for rotatably retaining said gear shaft in the head housing, and
a fixing member for fixing the retaining member in the head housing,
wherein said dust control seal is an annular member, and has a seal body, a first lip projecting radially inwardly from the seal body, and a second lip projecting radially inwardly from the seal body above and spaced apart from said first lip,
wherein said first and second lips define a space between a contact area between the first lip and the shaft part and a contact area between the second lip and the shaft part, and
wherein said dust control seal is held between the retaining member and the fixing member.

2. The dental handpiece according to claim 1, wherein said dust control seal is made of a rubber material.

3. The dental handpiece according to claim 2, wherein said hard coating is selected from the group consisting of diamond-like carbon (DLC), CrN, TiN, and TiCN.

4. The dental handpiece according to claim 1, wherein said shaft part of the gear shaft is provided with hard coating.

* * * * *